United States Patent [19]

Umezawa et al.

[11] Patent Number: 4,511,509

[45] Date of Patent: Apr. 16, 1985

[54] 3-ALKYLIDINE AZETIDINE COMPOUND AND THEIR PRODUCTION

[76] Inventors: Hamao Umezawa, Tokyo; Masaji Oono, Kamakura; Hiroshi Ishihama, Higashi-Murayama; Yoshinori Kyotani, Higashi-Yamato; Yoshio Takahashi, Higashi-Murayama, all of Japan

[73] Assignee: Kowa Co. Ltd, Nagoya-chi, Japan

[21] Appl. No.: 477,369

[22] Filed: Mar. 21, 1983

[30] Foreign Application Priority Data

Mar. 25, 1982 [JP] Japan .................................. 57-47829
May 14, 1982 [JP] Japan .................................. 57-81195

[51] Int. Cl.³ ...................... C07F 7/18; C07D 205/08; C07D 487/04; A61K 31/40
[52] U.S. Cl. .......................... 260/239 A; 260/245.2 T; 544/316
[58] Field of Search .................................. 260/239 A

[56] References Cited

PUBLICATIONS

Moriconi et al., J.A.C.S., 88, 3657, (1966).
Corbett et al., Chem. Abs. 92, 215268, 215270, (1979).
Kamatanie et al., *Heterocycles*, vol. 20, pp. 505–507, (1983).

*Primary Examiner*—Mark L. Berch
*Attorney, Agent, or Firm*—Oblon, Fisher, Spivak, McClelland & Maier

[57] ABSTRACT

An azetidine derivative of the formula,

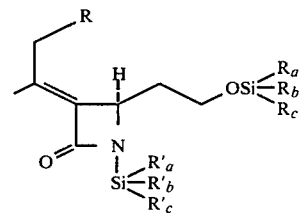

wherein R is a hydrogen atom or a hydroxyl group, and $R_a$, $R_b$, $R_c$, $R_a'$, $R_b'$ and $R_c'$ are identical or different and each are a lower alkyl group.

1 Claim, No Drawings

3-ALKYLIDINE AZETIDINE COMPOUND AND THEIR PRODUCTION

BACKGROUND OF THE INVENTION

1. Field of the Invention

This invention relates to novel azetidine derivatives, and more specifically to azetidine derivatives represented by the following formula (I),

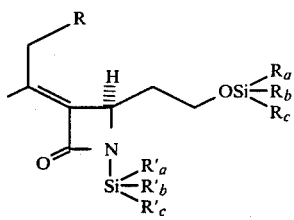
(I)

wherein R represents a hydrogen atom or a hydroxyl group, and $R_a$, $R_b$, $R_c$, $R_a'$, $R_b'$ and $R_c'$ are identical or different and each represent a lower alkyl group. Further, the invention is concerned with a process for producing such azetidine derivatives.

2. Description of the Prior Art

Carbapenem compounds have in recent years come into the limelight by reason of the fact that thienamycin discovered from the natural world exhibits strong antibacterial activity and β-lactamase inhibitory effect (see Japanese Laid-Open Application No. 73191/1976). In fact, this leads to subsequent publication of numerous compounds analogous to such carbapenem compounds. However, these compounds are all unstable and induce low productivity when produced by fermentation, and hence, are still far from actually useful.

With the foregoing difficulties of the existing techniques in view, the present inventors have carried out extensive study with a view toward preparing compounds of the above-described type by synthesis. As a result, they have succeeded in synthesizing novel β-lactam compounds having antibacterial activities and represented by the following formula (II),

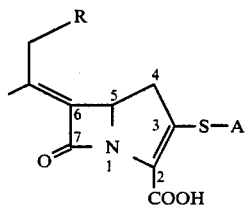
(II)

wherein A means an alkyl group, aryl group, residual group of a heterocyclic ring or the like.

SUMMARY OF THE INVENTION

Accordingly, it is an object of the present invention to provide the compounds of the formula (I) above which are important as intermediates for the preparation of the compounds represented by the formula (II).

Another object of the invention is to provide a process for the production of the compounds of the formula (I).

Briefly, these objects and other objects of the invention as hereinafter will become more readily apparent can be attained by providing an azetidine derivatives of the formula (I),

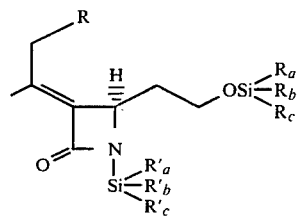

wherein R represents a hydrogen atom or a hydroxyl group, and $R_a$, $R_b$, $R_c$, $R_a'$, $R_b'$ and $R_c'$ are identical or different and each represent a lower alkyl group.

DETAILED DESCRIPTION OF THE PREFERRED EMBODIMENTS

The azetidine derivatives (I) of the present invention may be roughly divided, in accordance with the type of R, into the following groups of compounds (Ia) and compounds (Ib):

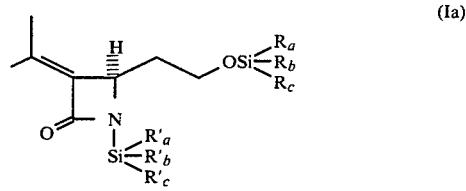
(Ia)

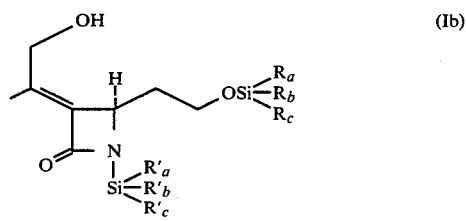
(Ib)

wherein all the symbols are as defined above.

In accordance with the invention, the compounds of the formula (I) may be prepared by the following reaction formulae:

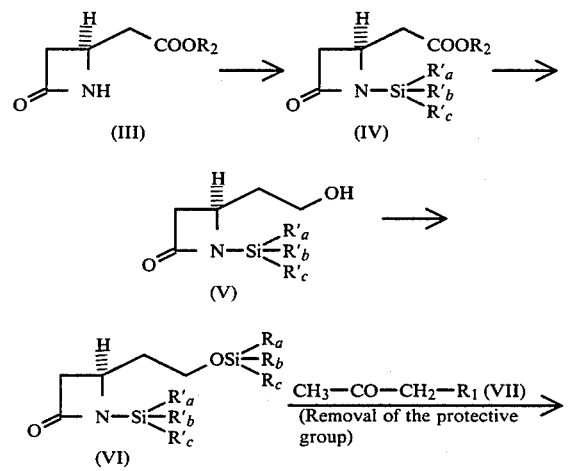

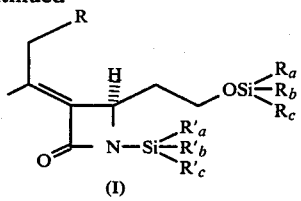

(I)

wherein $R_1$ is a hydrogen atom or a protected hydroxyl group, $R_2$ is a lower alkyl group, and the other symbols are as defined above.

The starting compound (III) may be readily prepared, for example, with use of dialkyl 3-ketoglutarate which is comparatively inexpensive by the procedure proposed by Ohno et al in J. Am. Chem. Soc., 103, 2406(1981).

Each of the reactions for the above-described process of the invention will now be described in detail.

1 (III)→(IV):

The compound (IV) is obtained by reacting 1 to 3 equivalents of a trialkylsilyl halogenide, preferably t-butyl dimethylsilyl chloride, with the compound (III). The reaction is preferably conducted in a solvent and in the presence of a base. Dimethylformamide, tetrahydrofuran or the like and a tertiary amine such as triethylamine or n-butyl lithium may be employed respectively as the solvent and base. The reaction may be completed in several minutes to several hours at a temperature ranging from −30° C. to +20° C.

2 (IV)→(V):

Reduction of the compound (IV) gives the compound (V).

It is preferred to carry out the reduction by using a reducing agent such as a metal aluminium hydride, e.g., lithium aluminium hydride, or a metal boron hydride, e.g., sodium borohydride or lithium borohydride. The reaction as well as the isolation and purification may be effected in a manner commonly used in the art.

3 (V)→(VI):

The compound (VI) can be obtained by causing a trialkylsilyl halogenide, preferably t-butyl dimethylsilyl chloride, to act on the compound (V). The reaction is preferably conducted in a solvent and in the presence of a base. Eligible solvents include dimethylformamide, pyridine or the like. On the other hand, eligible bases include a tertiary amine such as triethyl amine, imidazole, pyridine or the like.

4 (VI)→(I):

The compound (I) is obtained by, after activating the compound (VI) at its third position, causing a trialkylsilyl halogenide to act on the thus activated compound (VI) to form a 3-trialkylsilyl compound and then reacting the compound (VII) with an enolate of the 3-trialkylsilyl compound, and if desired, removing the protective group. In order to activate the compound (VI) at its third position, the compound (VI) may for example be reacted with lithium diisopropylamide at low temperatures in a solvent, e.g., tetrahydrofuran. It is preferred to carry out the reaction between the thus activated compound (VI) and a silyl compound, e.g., trimethylsilyl chloride at low temperatures, for example, from −100° C. to −50° C. and in a solvent, for example, tetrahydrofuran. The thus obtained compound is further lithiated and then reacted with the compound (VII). As the protective group $R_1$ for the hydroxyl group in the formula (VII), it is preferred to choose a group which is stable under alkalline conditions and readily removable. Eligible protective groups include methylthiomethyl group, p-methoxybenzyl group, 3,4-dimethoxybenzoyl group, methoxyethoxymethyl group and the like. It is preferable to carry out this reaction in a solvent similar to that mentioned above and at low temperatures similar to the above-described reactions. More conveniently, these two reactions can be performed in one pot uninterruptedly without isolating the 3-trialkylsilyl compound.

The removal reaction of the protective group $R_1$ can be effected in various ways. For example, (a) where a methylthiomethyl group is used as the protective group, it may be removed by reaction with mercuric chloride and calcium carbonate or cadmium carbonate, by treatment with methyl iodide and sodium hydrogencarbonate, or by reaction with silver nitrate and 2,6-lutidine, (b) where a p-methoxybenzyl or 3,4-dimethoxybenzyl group is employed as the protective group, it may be removed by treatment with 2,3-dichloro-5,6-dicyano-p-benzoquione, or (c) where a methoxyethoxymethyl group is used as the protective group, it may be removed by reaction with zinc bromide or titanium tetrachloride.

Since the process of this invention permits the final compound, i.e., the 3(E) isomer to be prepared with good selectivity and high yield, the final compound (II) which is the 6(E) isomer can be prepared efficiently.

Alternatively, the compounds (Ib) may be prepared by hydroxylating the compounds (Ia). This hydroxylation can be effected, for example, by oxidizing the compounds (Ia) with selenium dioxide and then reducing the thus oxidized compounds using a reducing agent such as sodium borohydride.

The compound (II) may be prepared from the compound (Ib), for example, in accordance with the following reaction scheme:

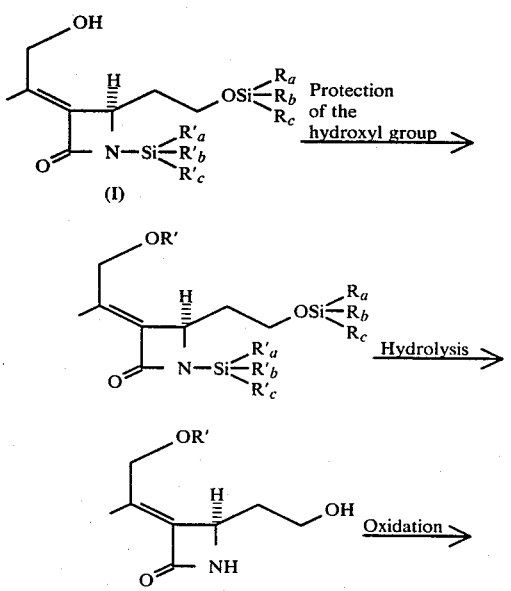

-continued

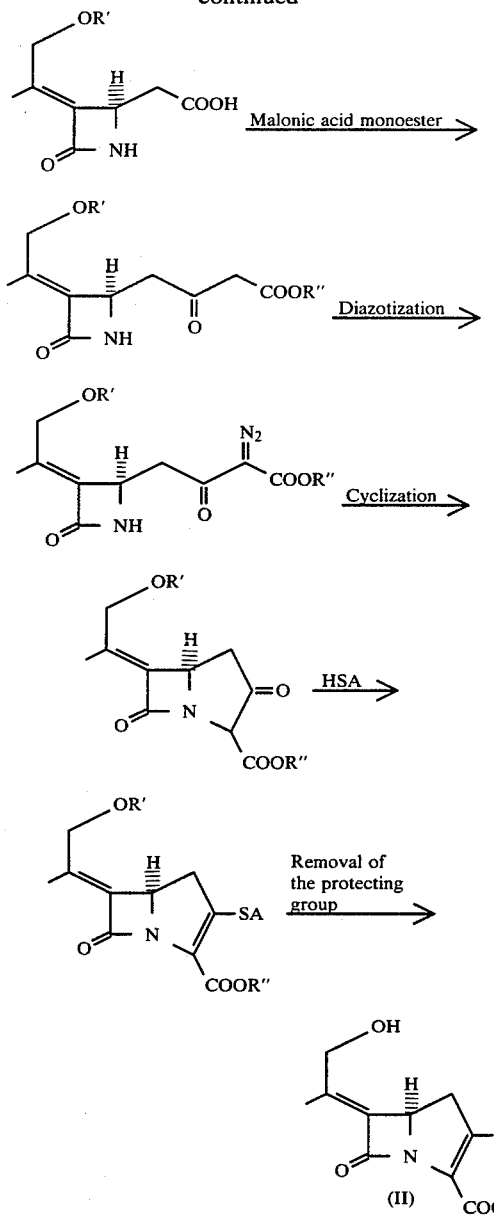

wherein R' is a protective group for the hydroxyl group and R" is a benzyl group which may optionally contain one or more substituent groups.

Among the compounds of the formula (II), those containing a 2-pyrimidyl group for A have such antibacterial activities as shown in the Table below.

TABLE

| Bacterium | MIC (mcg/ml) |
| --- | --- |
| *Streptococcus aureus* 209p JC-1 | 0.05 |
| *Streptococcus aureus* Smith | 0.2 |
| *Bacillus subtilis* ATCC 6633 | 0.78 |
| *Escherichia coli* NIHJ JC-2 | 0.39 |
| *Klebsiella pneumoniae* PCO 602 | 0.39 |
| *Serratia marcescens* NHL | 0.78 |
| *Proteus inconstans* 93 | 0.2 |
| *Proteus vulgaris* IID874 | 0.05 |
| *Salmonella typhi* H - 901 | 0.2 |
| *Pseudomonas aeruginosa* NCTC 10490 | 1.56 |
| *Pseudomonas putida* IID 5121 | 100 |
| *Escherichia coli* RECl (PC ase I) | 0.39 |

TABLE-continued

| Bacterium | MIC (mcg/ml) |
| --- | --- |
| *Escherichia coli* 59 (PC ase II) | 0.2 |
| *Escherichia coli* 68 (PC ase IV) | 0.2 |
| *Proteus inconstans* 113 | 0.78 |

The above disclosure generally describes the present invention. A more complete understanding can be obtained by reference to the following specific examples which are provided herein for purposes of illustration and are not intended to be limiting.

EXAMPLE 1

(a) Preparation of (4S)-1-(t-butyldimethylsilyl)-4-(methoxycarbonylmethyl)-azetidine-2-one:

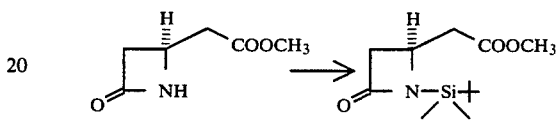

To a stirred solution of 2.0 g of (4S)-4-(methoxycarbonylmethyl)-azetidine-2-one which had been prepared according to the procedure described in J. Am. Chem. Soc., 103, 2405(1981) and 2.56 ml of triethylamine in 30 ml of dimethylformamide was added 2.74 g of t-butyldimethylchlorosilane at 0° C. The thus obtained mixture was stirred for further 50 minutes. After completion of the reaction, dimethylformamide was removed under reduced pressure and the residue was dissolved in methylene chloride and washed with water. The methylene chloride solution was dried and concentrated. The residue was purified by silica gel column chromatography (solvent: a 5:1 mixture of n-hexane and ethyl acetate) to give 3.47 g of the intended product as colorless crystals (yield: 96.8%).

Specific rotation: $[\alpha]_D^{25} - 80.0°$ (c 1.0, THF)
IR $\nu_{max}^{CHCl_3}$ cm$^{-1}$: 1743, 1735
PMR δCDCl$_3$ ppm: 0.20(3H,s), 0.23(3H,s), 0.93(9H,s); 2.47(1H,dd,J=16 Hz,10 Hz); 2.76(1H,dd,J=16 Hz,3 Hz); 2.85(1H,dd,J=15 Hz,5 Hz); 3.28(1H,dd,J=15 Hz,6 Hz); 3.68(3H,s), 3.88(1H,m).

(b) Preparation of (4R)-1-(t-butyldimethylsilyl)-4-(2-hydroxyethyl)-azetidine-2-one:

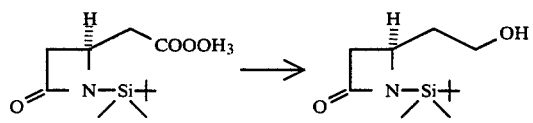

Lithium aluminum hydride (270 mg) was suspended in 70 ml of anhydrous ether, and the suspension was cooled to −20° C. under a nitrogen atmosphere and stirred, into which was dropped a solution of 1.42 g of the ester obtained in Example 1(a) in 70 ml of anhydrous ether. The resultant mixture was stirred for 10 minutes at −20° C. After decomposing excess reagents by addition of 2N-HCl, the resultant reaction mixture was extracted with ether. The extract was washed with water and dried. Evaporation of the solvent gave 1.23 g of the intended product as a colorless oil (yield: 97.2%).

Specific rotation: $[\alpha]_D^{25} - 71.0°$ (c 1.0, THF)
IR $\nu_{max}^{CHCl_3}$ cm$^{-1}$: 3630, 3420(shoulder), 1725

PMR δCDCl₃ ppm: 0.23(6H,s), 0.96(9H,s), 1.7(1H,m); 1.83(1H, broad s), 212(1H,m); 2.72(1H,dd,J=15 Hz,3 Hz); 3.17(1H,dd,J=15 Hz,5 Hz), 3.68(1H,m); 3.74(2H,t,J=7 Hz).

(c) Preparation of (4R)-1-(t-butyldimethylsilyl)-4-(2-t-butyldimethylsilyloxyethyl)-azetidine-2-one:

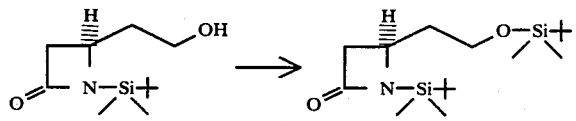

To a stirred solution of 1.23 g of the alcohol obtained in Example 1(b) and 0.83 ml of triethylamine in 18 ml of dimethylformamide was added 886 mg of t-butyldimethylchlorosilane at 0° C. The reaction mixture was stirred at room temperature for 35 minutes. The solvent was removed under reduced pressure, and the residue was dissolved in ether. The ether solution was washed with water, dried and then concentrated. The thus obtained residue was purified by silica gel column chromatography (solvent: methylene chloride) to give 1.54 g of the intended product as a colorless oil (yield: 83.4%).

Specific rotation: $[\alpha]_D^{25}$ −63.0° (c 1, THF)
IR $\nu_{max}^{CHCl_3}$ cm⁻¹: 1724
PMR δCDCl₃ ppm: 0.03(6H,s), 0.23(6H,s), 0.88(9H,s); 0.97(9H,s), 1.64(1H,m), 2.06(1H,m); 2.72(1H,dd,J=16 Hz,2 Hz); 3.11(1H,dd,J=16 Hz,5 Hz). 3.65(1H,m), 3.68(2H,t,J=16 Hz).

(d) Preparation of (4R)-1-(t-butyldimethylsilyl)-3(E)-[1-methyl-2-(methylthiomethyl)oxyethylidene]-4-(2-t-butyldimethylsilyloxyethyl)-azetidine-2-one:

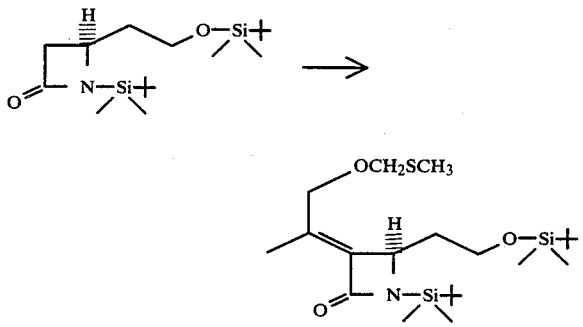

To a stirred solution of diisopropylamine (0.297 ml) in anhydrous tetrahydrofuran (3.57 ml) was added 1.32 ml of n-butyl lithium (as a 1.6M solution in hexane) at −78° C. under a nitrogen atmosphere. Ten minutes later, a solution of the disilyl derivative (160.7 mg) obtained in Example 1(c) in anhydrous tetrahydrofuran (2.95 ml) was added slowly and dissolved. After being stirred for 10 minutes, the mixture was stirred for further 15 minutes at −50° C. The reaction mixture was cooled again to −78° C. and added with a solution of trimethylsilane chloride (0.0657 ml) in anhydrous tetrahydrofuran (0.66 ml). The resultant mixture was stirred for 10 minutes and then for further 15 minutes at −50° C. The reaction mixture was cooled once more to −78° C. and added with a solution of 1-(methylthiomethyl)oxypropan-2-one (509 mg) in anhydrous tetrahydrofuran (1.78 ml). After stirring the thus formed mixture for 15 minutes, 2.14 ml of a saturated aqueous solution of ammonium chloride was added. The mixture was then heated at 40° C. for 20 minutes. The reaction mixture was extracted with methylene chloride, and the extract was washed with water and dried. Evaporation of the solvent gave 590 mg of a colorless oil substance. The substance was purified by silica gel column chromatography (solvent: a 4:1 mixture of n-hexane and ethyl acetate) to give 179 mg of the intended product as a colorless oil (yield: 83.3%).

Specific rotation: $[\alpha]_D^{27}$ −20.9° (c 3.3, THF)
IR $\nu_{max}^{CHCl_3}$ cm⁻¹: 1720
PMR δCDCl₃ ppm: 0.04(6H,s), 0.24(3H,s), 0.28(3H,s) 0.89(9H,s), 0.98(9H,s); 1.8-2.2(2H, complex m), 2.05(3H,s); 2.15(3H,s), 3.71(2H,t,J=7 Hz), 4.03(2H,s), 4.30(1H,m), 4.62(2H,s).

(e) Preparation of (4R)-1-(t-butyldimethylsilyl)-3(E)-(1-methyl-2-hydroxy)ethylidene-4-(2-t-butyldimethylsilyoxyethyl)-azetidine-2-one:

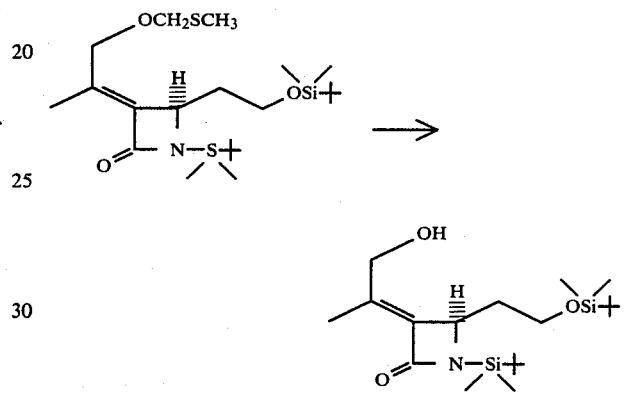

To a stirred solution of 477 mg of the methylthiomethyl derivative obtained in Example 1(d) in 25 ml of a 4:1 mixture of acetonitrile and water were added 565 mg of mercuric chloride and 314 mg of calcium carbonate. The mixture was stirred for 10 hours at 50° C. In the course of reaction, 565 mg of mercuric chloride was further added twice at such time that 2 hours and 4 hours had elapsed. The reaction mixture was filtered, and undissolved matter was washed with ethyl acetate. The filtrate and washings were combined together, washed with brine, dried and then concentrated to give 700 mg of an oily substance. The substance was purified by silica gel chromatography (solvent: a 6:1 mixture of n-hexane and ethyl acetate) to yield 337 mg of the intended product as colorless crystals (yield: 81.3%).

IR $\nu_{max}^{CDCl_3}$ cm⁻¹: 1720
PMR δCDCl₃ ppm: 0.06(6H,s), 0.21(3H,s) 0.25(3H,s), 0.90(9H,s) 0.97(9H,s), 1.60-2.19(2H, complex m); 2.02(3H,s), 3.22(1H,broad t,J=6 Hz); 3.77(2H,t,J=6 Hz), 4.10(2H,d,J=6 Hz); 4.40(1H,m).

EXAMPLE 2

To a stirred solution of 25 mg of the methylthiomethyl derivative obtained in Example 1(d) in 0.2 ml of acetone were added 0.05 ml of methyl iodide and 30 mg of sodium hydrogencarbonate. The resultant mixture was stirred for 5 days at room temperature. The reaction mixture was concentrated and then added with methylene chloride. After being washed with water, the mixture was dried and concentrated. The residue was purified by silica gel column chromatography (solvent: a 3:1 mixture of n-hexane and ethyl acetate) to give 11 mg of the intended alcohol as colorless crystals (yield:

50.6%). The IR and PMR data of the product were in agreement with those of the alcohol obtained in Example 1.

EXAMPLE 3

(a) Preparation of (4R)-1-(t-butyldimethylsilyl)-3(E)-[1-methyl-2-(p-methoxybenzyl)oxyethylidene]-4-(2-butyldimethylsilyloxyethyl)-azetidine-2-one:

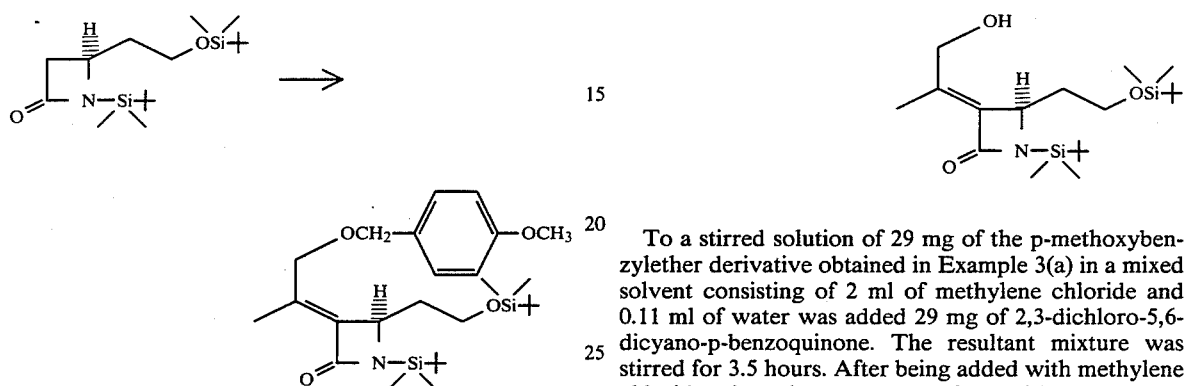

To a stirred solution of diisopropylamine (0.0795 ml) in anhydrous tetrahydrofuran (0.955 ml) was added 0.365 ml of n-butyl lithium (as a 1.6M solution in hexane) at −78° C. under a nitrogen atmosphere. After the resultant mixture was stirred for 10 minutes, 42.97 mg of the disilyl derivative obtained in Example 1(c) in 0.8 ml of anhydrous tetrahydrofuran was dropped. The mixture was stirred for 10 minutes and then for further 15 minutes at −50° C. The reaction mixture was cooled again to −78° C. and added with 0.0175 ml of trimethylchlorosilane in 0.18 ml of anhydrous tetrahydrofuran. Subsequently to stirring for 10 minutes, the mixture was stirred for further 15 minutes at −50° C. The reaction mixture was cooled again to −78° C. and added with 197 mg of p-methoxybenzyloxypropane-2-one in 0.48 ml of anhydrous tetrahydrofuran. The thus formed mixture was stirred for 15 minutes and added with 0.57 ml of a saturated aqueous solution of ammonium chloride. The resultant mixture was heated at 40° C. for 20 minutes. The reaction mixture was extracted with methylene chloride, and the extract was washed 2 with water, dried and then concentrated to 250 mg of an oily substance. The substance was purified by silica gel column chromatography (solvent: a 4:1 mixture of n-hexane and ethyl acetate) to give 52 mg of the intended product as a colorless oil (yield: 80.0%).

IR $\nu_{max}^{CHCl_3}$ cm$^{-1}$: 1720, 1610, 1515

PMR $\delta CDCl_3$ ppm: 0.02(6H,s), 0.22(3H,s), 0.27(3H,s) 0.87(9H,s), 0.96(9H,s); 1.6–2.15(2H,complex m), 2.04(3H,s); 3.66(2H,t,J=7 Hz), 3.80(3H,s); 3.94(2H,s), 4.26(1H,m), 4.42(2H,s); 6.86(2H,d,J=8 Hz), 7.24(2H,d,J=8 Hz).

(b) Preparation of (4R)-1-(t-butyldimethylsilyl)-3(E)-(1-methyl-2-hydroxy)ethylidene-4-(2-t-butyldimethylsilyloxyethyl)-azetidine-2-one:

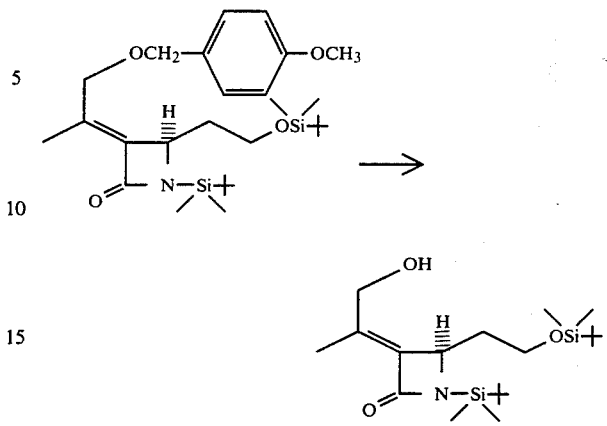

To a stirred solution of 29 mg of the p-methoxybenzylether derivative obtained in Example 3(a) in a mixed solvent consisting of 2 ml of methylene chloride and 0.11 ml of water was added 29 mg of 2,3-dichloro-5,6-dicyano-p-benzoquinone. The resultant mixture was stirred for 3.5 hours. After being added with methylene chloride, the mixture was washed with a saturated NaHCO$_3$ solution. The thus formed mixture was dried and concentrated, and the resultant brownish oily substance was purified by silica gel chromatography (solvent: a 3:1 mixture of n-hexane and ethyl acetate) to give 12 mg of the intended product as colorless crystals (yield: 53.9%). The IR and PMR data of the product were agreement with those of the alcohol obtained in Example 1.

EXAMPLE 4

(a) Preparation of (4R)-1-(t-butyldimethylsilyl)-3(E)-[1-methyl-2-(methoxyethyoxymethyl)oxyethylidene]-4-(2-t-butyldimethylsilyloxyethyl)-azetidine-2-one:

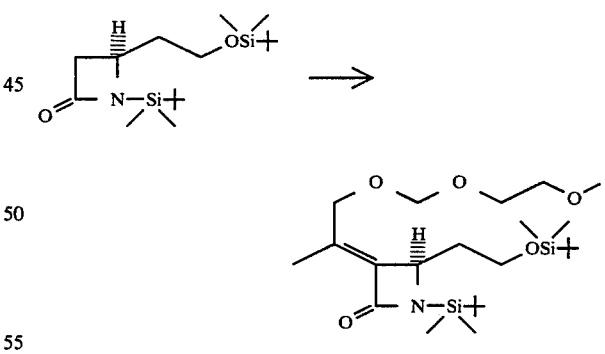

Diisopropylamine (0.178 ml) and anhydrous tetrahydrofuran (3.5 ml) were placed in a flask, cooled to −78° C. and then stirred under a nitrogen atmosphere. Thereafter, 0.814 ml of n-butyl lithium (as a 1.6M solution in hexane) was added. The resultant mixture was stirred for 10 minutes, followed by dropwise addition of 95.7 mg of the disilyl derivative obtained in Example 1(c) in 2.4 ml of anhydrous tetrahydrofuran. The mixture was stirred for 10 minutes and then for further 15 minutes at −50° C. The reaction mixture was cooled again −78° C. and added with a solution of 0.0382 ml of trimethylchlorosilane in 0.36 ml of anhydrous tetrahydrofuran.

The thus formed mixture was stirred for 10 minutes and then for further 15 minutes at −50° C. The reaction mixture was cooled once more to −78° C. and added with a solution of 210 mg of 1-(methoxyethoxymethyl-)oxypropane-2-one in 0.52 ml of anhydrous tetrahydrofuran. The resultant mixture was stirred for 15 minutes. Thereafter, 1.28 ml of a saturated aqueous solution of ammonium chloride was added, and the resultant mixture was stirred for 20 minutes at 40° C. The reaction mixture was extracted with ethyl acetate, and the extract was dried and concentrated to 240 mg of a colorless oily substance. The substance was purified by silica gel column chromatography (solvent: a 2:1 mixture of n-hexane and ethyl acetate) to give 77.4 mg of the intended product as a colorless oil (yield: 58.5%).

IR $\nu_{max}^{Film}$ cm$^{-1}$: 2930, 2860, 1720

PMR δCDCl$_3$ ppm: 0.01(6H,s), 0.20(3H,s), 0.25(3H,s); 0.84(9H,s), 0.95(9H,s); 1.90–2.05(2H,m), 2.02(3H,s); 3.35(3H,s), 3.45–3.76(6H,complex m); 4.01(2H,s), 4.25(1H,t,J=5 Hz); 4.67(2H,s).

EXAMPLE 5

Preparation of (4R)-1-(t-butyldimethylsilyl)-3-isopropylidene-4-(2-t-butyldimethylsilyloxyethyl)-azetidine-2-one:

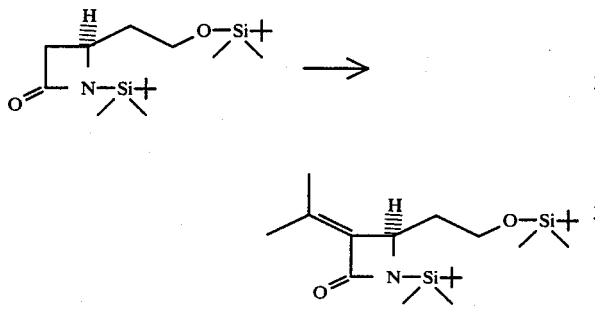

To a stirred solution of 0.207 ml of diisopropylamine in 2.5 ml of anhydrous tetrahydrofuran was added dropwise 0.922 ml of n-butyl lithium (as a 1.6M solution in hexane) at −78° C. under a nitrogen atmosphere. The resultant mixture was stirred for 10 minutes. Thereafter, 112 mg of the disilyl derivative obtained in Example 1(c) in 1.5 ml of anhydrous tetrahydrofuran was dropped. After being stirred for 10 minutes, the mixture was stirred further at −50° C. for 15 minutes. The reaction mixture was cooled again to −78° C. and added with 0.045 ml of trimethylchlorosilane. The resultant mixture was stirred for 10 minutes and then for further 15 minutes at −50° C. The reaction mixture was cooled once more to −78° C. and added with 0.185 ml of acetone. After stirring the resultant mixture for 15 minutes, 1.5 ml of a saturated aqueous solution of ammonium chloride was added. The mixture was heated at 40° C. for 20 minutes. The reaction mixture was extracted with methylene chloride, and the extract was washed with water, dried and evaporated. The residue was purified by silica gel column chromatography (solvent: a 15:1 mixture of methylene chloride and ether) to give 130 mg of the intended product as a colorless oil. The thus obtained product contained 25% of a 3-trimethylsilyl compound.

IR $\nu_{max}^{CHCl_3}$ cm$^{-1}$: 1710

PMR δCDCl$_3$ ppm: 0.03(6H,s), 0.20(3H,s), 0.24(3H,s); 0.83(9H,s), 0.94(3H,s); 1.4–2.2(2H,complex m), 1.72(3H,s); 2.00(3H,s), 3.67(2H,t,J=7 Hz); 4.20(1H,t,J=5 Hz).

EXAMPLE 6

Preparation of (4R)-1-(t-butyldimethylsilyl)-3(Z and E)-(1-methyl-2-hydroxy)ethylidene-4-(2-t-butyldimethylsilyl)-oxyethyl-azetidine-2-one:

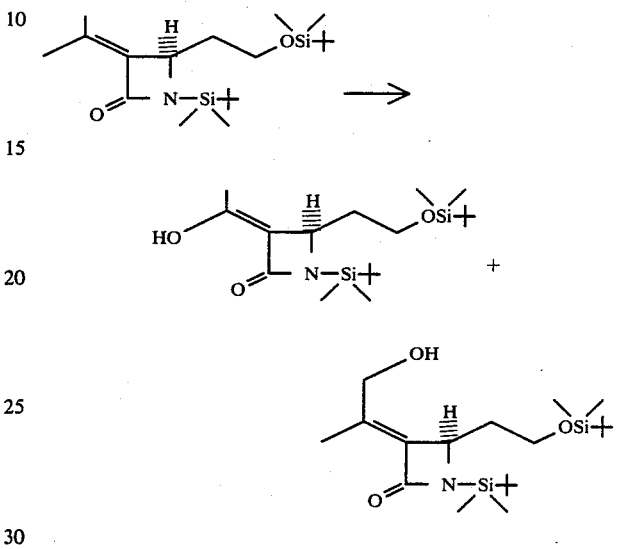

To a stirred solution of 984 mg of the isopropylidene derivative (which contained 25% of the 3-trimethylsilyl compound and was obtained in Example 5) in 20 ml of dioxane were added dropwise a solution of 218 mg of selenium dioxide dissolved in 12 ml of a 5:1 liquid mixture of dioxane and water at 105° C. The resultant mixture was stirred for 41.5 hours. In the course of stirring, an aqueous dioxane solution of selenium dioxide was added in the same amount as added above upon expiration of 14 hours. After completion of the reaction, undissolved matter was removed by filtration. The filtrate was concentrated, and the residue was dissolved in ethyl acetate. The solution was washed with water and then with a saturated NaHCO$_3$ solution, and the resultant mixture was dried and concentrated to give 1.0 g of a yellowish oily substance. The substance was then dissolved in methanol and added with 40 mg of sodium borohydride at 0° C. The resultant mixture was stirred for 70 minutes. The reaction mixture was concentrated, and the residue was dissolved in ethyl acetate. After being washed with water, the ethyl acetate solution was dried and concentrated to give 1.0 g of a brownish oily substance. The substance was purified by silica gel column chromatography (solvent: a 6:1 mixture of n-hexane and ethyl acetate) to give 270 mg of the Z-isomer (yield: 35.3%) and 110 mg of the E-isomer (yield: 14.4%) as colorless oils.

Z-Isomer:

IR $\nu_{max}^{CHCl_3}$ cm$^{-1}$: 3340(broad), 1695

PMR δCDCl$_3$ ppm: 0.04(6H,s), 0.26(3H,s), 0.30(3H,s); 0.70(9H,s), 0.98(9H,s), 1.72(3H,s); 1.60–2.06(2H,complex m); 3.72(2H,t,J=6 Hz), 4.25(3H,complex m).

E-Isomer:

IR $\nu_{max}^{CHCl_3}$ cm$^{-1}$: 1720

PMR δCDCl₃ ppm: 0.06(6H,s), 0.21(3H,s), 0.25(3H,s); 0.90(9H,s), 0.97(9H,s); 1.60–2.19(2H,complex m); 2.02(3H,s), 3.77(2H,t,J=6 Hz); 4.10(2H,s), 4.40(1H,m).

Referential Example

Preparation of (5R)6(E)-(1-methyl-2-hydroxyethylidene)-3-(2-pyrimidinylthio)-1-azabicyclo[3.2.0-]hept-2-en-7-one-2-carboxylic acid:

(a) Preparation of (4R)-1-(t-butyldimethylsilyl)-3(E)-[1-methyl-2-(p-nitrobenzyl)oxycarbonyloxyethylidene]-4-(2-t-butyldimethylsilyloxyethyl)-azetidine-2-one:

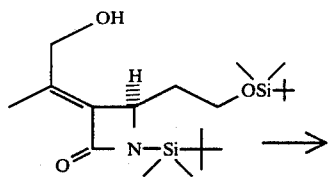

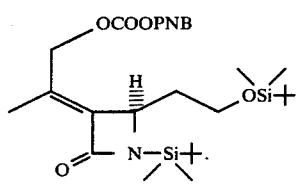

The E-alcohol (309 mg) obtained in Example 1 was dissolved in 5 ml of methylene chloride, cooled to 0° C. under a nitrogen atmosphere and then added with 142 mg of 4-dimethylaminopyridine. Thereafter, a solution of 250 mg of p-nitrobenzyl chloroformate in 2 ml of methylene chloride was added. The resultant mixture was stirred with ice cooling for 6 hours. In the course of stirring, 4-dimethylaminopyridine and a methylene chloride solution of p-nitrobenzyl chloroformate were added in the same amounts as added above upon expiration of 3.5 hours and 5 hours, respectively. Methylene chloride was then added to the reaction mixture. The resultant mixture was washed with water, dried and then concentrated to give 1.0 g of a yellowish oily substance. Purification of the substance by silica gel column chromatography (solvent: a 2:5 mixture of ethyl acetate and n-hexane) gave 390 mg of the intended product (yield: 87.2%).

IR $\nu_{max}^{CHCl_3}$ cm⁻¹: 1750, 1735, 1610, 1530

PMR δCDCl₃ ppm: 0.03(6H,s), 0.22(3H,s), 0.25(3H,s); 0.84(9H,s), 0.98(9H,s); 1.81–2.13(2H,m), 2.05(3H,s); 3.68(2H,t,J=6 Hz), 4.32(1H,t,J=4 Hz); 4.62(2H,s), 5.24(1H,s), 5.26(1H,s); 7.50(2H,d,J=9 Hz), 8.19(2H,d,J=9 Hz).

(b) Preparation of (4R)-3(E)-[1-methyl-2-(p-nitrobenzyl)oxycarbonyloxyethylidene]-4-(2-hydroxyethyl)-azetidine-2-one:

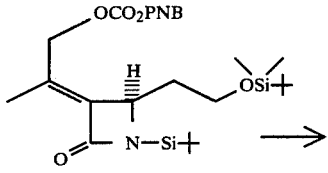

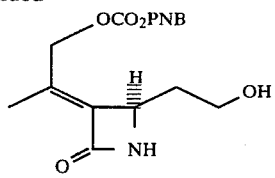

To a stirred solution of 390 mg of the disilyl derivative obtained in (a) above in 14 ml of a 90% aqueous methanol solution was added dropwise with ice cooling 0.24 ml of conc. hydrochloric acid. The resultant mixture was stirred with ice cooling for 2 hours and for further 5 hours. A saturated NaHCO₃ solution was added to the reaction mixture to adjust its pH to 7. After concentrating the pH-adjusted mixture, the residue was dissolved in ethyl acetate, and the resultant solution was dried and concentrated. The residue was purified by silica gel column chromatography (solvent: a 7:1 mixture of chloroform and methanol) to give 220 mg of the intended product as colorless crystals (yield: 93.2%).

IR $\nu_{max}^{KBr}$ cm⁻¹: 3400(broad), 1750, 1710, 1610, 1540

PMR δCDCl₃–CD₃OD(6:1) ppm: 1.59–2.21(2H,m), 2.05(3H,s); 3.68(2H,t,J=6 Hz), 4.05(2H,s); 4.26(1H,dd,J=9 Hz,4 Hz), 4.63(2H,s) 5.25(2H,s), 7.52(2H,d,J=9 Hz) 8.20(2H,d,J=9 Hz).

(c) Preparation of (4R)3(E)-[1-methyl-2-(p-nitrobenzyl)-oxycarbonyloxyethylidene]-4-carboxymethyl-azetidine-2-one:

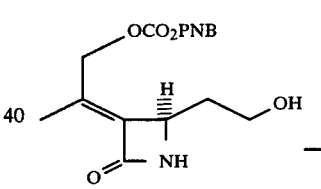

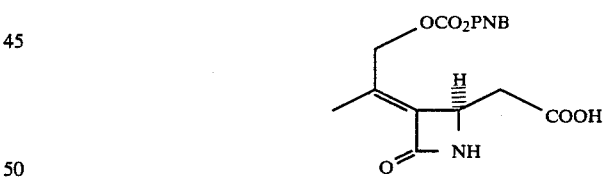

The alcohol (220 mg) obtained in (b) above was dissolved in 3 ml of pyridine, to which was added a solution of 490 mg of chromic anhydride in 6 ml of pyridine. The resultant mixture was stirred as room temperature for 14.5 hours. The reaction mixture was added with 10 ml of water and then extracted with ethyl acetate. After being dried, the extract was concentrated to give 276 mg of the intended product in crude form and as a brownish oil.

IR $\nu_{max}^{Film}$ cm⁻¹: 3240, 1750, 1600, 1520;

PMR δCDCl₃ ppm: 2.06(3H,broad s), 4.64(2H,broad s); 5.24(2H,broad s), 8.17(2H,broad s); 8.59(2H,broad s).

(d) Preparation of (4R)3(E)-[1-methyl-2-(p-nitrobenzyl)-oxycarbonyloxyethylidene]-4-[3-(p-nitrobenzyl)oxycarbonyl-2-oxypropyl]-azetidine-2-one:

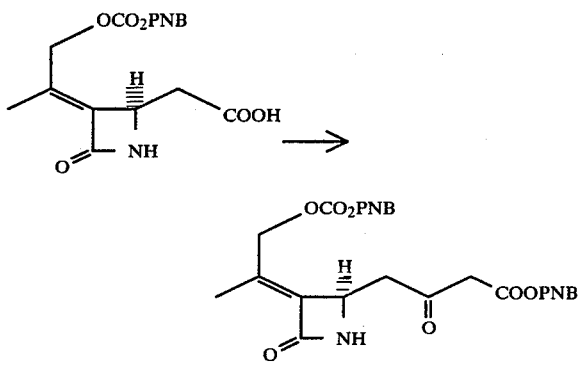

The crude carboxylic acid (276 mg) obtained in (c) above was dissolved in 4.8 ml of anhydrous tetrahydrofuran, to which was added 112 mg of N,N'-carbonyldiimidazole at room temperature under a nitrogen atmosphere. The resultant mixture was stirred for 2 hours at room temperature.

Meanwhile, to a solution of 245 mg of mono-p-nitrobenzyl malonate in 3.8 ml of anhydrous tetrahydrofuran was added 38.8 mg of magnesium methoxide under a nitrogen atmosphere. The resultant mixture was stirred for 1 hour and concentrated, and the residue was combined with the above-prepared imidazolide solution. The mixture was stirred at room temperature for 12 hours and concentrated. The residue was dissolved in a liquid mixture of ethyl acetate and 0.3N hydrochloric acid. The thus formed mixture was extracted with ethyl acetate. After being washed with a saturated NaHCO$_3$ solution, the extract was dried and evaporated to give a brownish oily substance. The substance was purified by silica gel column chromatography (solvent: a 10:1 mixture of chloroform and methanol) to give 175 mg of the intended product as colorless crystals [yield: 51.5% based on the weight of the product in (c) above].

IR $\nu_{max}^{Film}$ cm$^{-1}$: 3360(broad), 1740

PMR δCDCl$_3$ ppm: 2.10(3H,s), 2.83(1H,dd,J=18 Hz,9 Hz); 3.32(1H,dd,J=18 Hz,2 Hz), 3.50(1H,s); 4.40(1H,m), 4.55(1H,s), 4.63(1H,s); 5.22(4H,s), 6.50(1H,broad s); 7.47(4H,d,J=9 Hz), 8.15(4H,d,J=9 Hz).

(e) Preparation of (4R)3(E)-[1-methyl-2-(p-nitrobenzyl)oxycarbonyloxyethylidene]-4-[3-(p-nitrobenzyl)oxycarbonyl-2-oxo-3-diazopropyl]-azetidine-2-one:

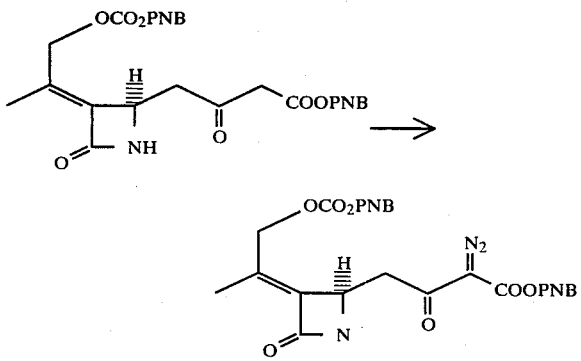

To a stirred solution of 175 mg of the β-ketoester obtained in (3) above in 5.8 ml of acetonitrile were added with ice cooling 83.9 mg of p-toluenesulfonyl azide and 95.2 mg of triethylamine. The resultant mixture was stirred at room temperature for 130 minutes. The reaction mixture was concentrated, and the residue was purified by silica gel column chromatography (solvent: a 1:1 mixture of ethyl acetate and chloroform) to give 176 mg of the intended product as a yellowish oil (yield: 96.0%).

IR $\nu_{max}^{Film}$ cm$^{-1}$: 3160(broad), 2130, 1740, 1645, 1605 1520;

PMR δCDCl$_3$ ppm: 2.04(3H,s), 3.02(1H,dd,J=18 Hz,9 Hz); 3.58(1H,dd,J=18 Hz,3 Hz), 4.48(1H,m); 4.62(2H,s), 5.22(2H,s), 5.30(2H,s); 6.68(1H,broad s), 7.47(4H,d,J=9 Hz); 8.16(4H,d,J=9 Hz).

(f) Preparation of (5R)p-nitrobenzyl-6(E)-[1-methyl-2-(p-nitrobenzyl)oxycarbonyloxyethylidene]-1-azabicyclo[3.2.0]-hepta-3,7-dione-2-carboxylate:

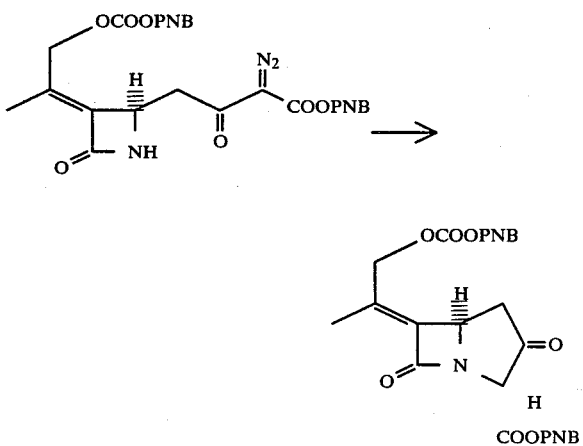

To a stirred solution of 176 mg of the diazo derivative obtained in (e) above in 9.5 ml of deaerated anhydrous benzene was added 0.3 mg of rhodium acetate under a nitrogen atmosphere. The thus formed mixture was stirred for 90 minutes at 78° C.

The reaction mixture was filtered, and the filtrate was concentrated to give 165 mg of the intended product as a yellowish oil (yield: 98.6%).

IR $\nu_{max}^{Film}$ cm$^{-1}$: 1750, 1605, 1520

PMR δCDCl$_3$ ppm: 2.08(3H,s), 2.44(1H,dd,J=18 Hz,7 Hz); 2.82(1H,dd,J=18 Hz,7 Hz); 4.62(1H,t,J=7 Hz), 4.70(3H,s); 4.74(1H,s), 5.24(4H,s); 7.50(4H,d,J=9 Hz), 8.18(4H,d,J=9 Hz).

(g) Preparation of (5R)p-nitrobenzyl-6(Z and E)-[1-methyl-2-(p-nitrobenzyl)oxycarbonyloxyethylidene]-3-(2-pyrimidinylthio)-1-azabicyclo[3.2.0]hept-2-en-7-one-2-carboxylate:

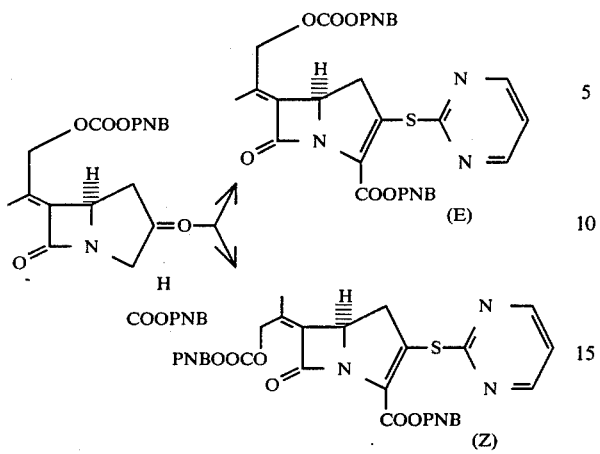

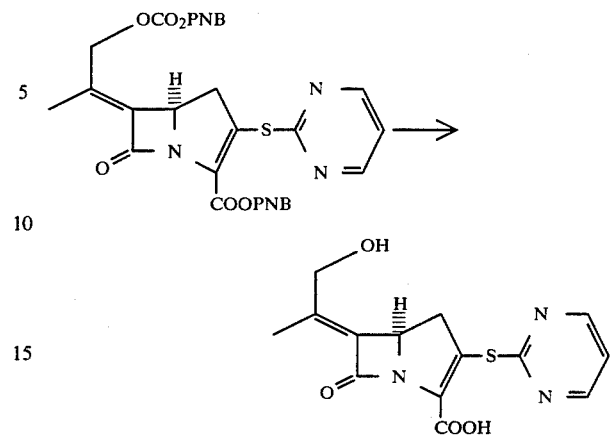

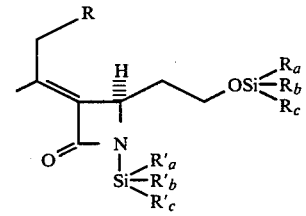

To a stirred solution of 74.0 mg of the bicycloketone obtained in (f) above in a mixture of 5.36 ml of acetonitrile and 0.4 ml of dimethylformamide was added with ice cooling 0.028 ml of diisopropylethylamine under a nitrogen atmosphere and then added an ice-cooled solution of 40.2 mg of diphenyl chlorophosphate in 0.1 ml of acetonitrile. The mixture was stirred with ice cooling for 10 minutes. The reaction mixture was cooled to −25° C. and added with 75.5 mg of diisopropylethylamine and 16.9 mg of 2-mercaptopyridmine. The resultant mixture was stirred at 0° C. for 30 minutes and allowed to stand for 17 hours in a refrigerator. Ethyl acetate was then added to the reaction mixture. After being washed with brine, the mixture was dried and concentrated. The residue was purified by silica gel column chromatography (solvent: a 30:1 mixture of chloroform and methanol) and then subjected to further isolation by silica gel column chromatography (solvent: a 3:1 mixture of ethyl acetate and n-hexane) to give 38.9 mg of the intended E-isomer (yield: 44.8%) and 10.4 mg of the Z-isomer (yield: 14.2%) as light yellowish oils.

Z-Isomer:

Specific rotation: $[\alpha]_D^{23}$ −79.0° (c 0.29, THF)
IR $\nu_{max}^{CHCl3}$ cm$^{-1}$: 3280(broad), 1760, 1610
PMR δCDCl$_3$ ppm: 1.85(3H,s), 3.18(1H,dd,J=18 Hz,9 Hz); 3.92(1H,dd,J=18 Hz,10 Hz), 4.82(1H,m); 5.04(2H,s), 5.25(2H,s); 5.27(1H,d,J=14 Hz), 5.53(1H,d,J=14 Hz); 7.05(1H,t,J=5 Hz), 7.50(2H,d,J=9 Hz); 7.62(2H,d,J=9 Hz), 8.19(4H,d,J=9 Hz); 8.55(2H,d,J=5 Hz).

E-Isomer:

Specific rotation: $[\alpha]_D^{23}$ −27.0° (c 1, THF)
IR $\nu_{max}^{CHCl3}$ cm$^{-1}$: 1770, 1720(shoulder), 1610
PMR δCDCl$_3$ ppm: 2.10(3H,s), 3.18(1H,dd,J=18 Hz,9 Hz); 3.82(1H,dd,J=18 Hz,10 Hz), 4.70(2H,s); 4.70-4.90(1H,m), 5.22(2H,s); 5.26(1H,d,J=14 Hz), 5.52(1H,d,J=14 Hz); 7.02(1H,t,J=5 Hz), 7.45(2H,d,J=9 Hz); 7.62(2H,d,J=9 Hz), 8.18(4H,d,J=9 Hz); 8.45(2H,d,J=5 Hz).

(h) Preparation of (5R)6(E)-(1-methyl-2-hydroxyethylidene)-3-(2-pyrimidinylthio)-1-azabicyclo[3.2.0-]hept-2-en-7-one-2-carboxylic acid:

To a stirred solution of 82.7 mg of the p-nitrobenzyl ester obtained in (g) above in a mixture of 3.5 ml of dioxane and 3.5 ml of a phosphate buffer of pH 7.0 was added 83 mg of 5% palladium carbon. The resultant mixture was stirred for 2 hours under a hydrogen atmosphere (1 atm.). The catalyst was removed by filtration, and the filtrate was washed with ethyl acetate. Thereafter, salt was added to the water layer until its concentration reached 5%. The solution was adsorbed on a column packed with 25 ml of "Dia-Ion HP-20" (trademark, Mitsubishi Chem. Ind. Co., Ltd.). The column was washed with water and eluted with a 30% aqueous methanol solution. Fractions containing the intended compound were collected. The fractions were concentrated and lyophilized to give 25.3 mg of the intended product as colorless powder (yield: 60.7%).

Specific rotation: $[\alpha]_D^{18}$ −186.7° (c 0.375, H$_2$O);
IR $\nu_{max}^{KBr}$ cm$^{-1}$: 3430(broad), 1740, 1610, 1560;
UV $\nu_{max}^{H2O}$ nm(ε): 239.5 (18,200);
PMR δD$_2$O ppm (supposing that D$_2$O was 4.80): 2.08(3H,s), 3.08(1H,dd,J=18 Hz,9 Hz); 3.45(1H,dd,J=18 Hz,10 Hz), 4.29(2H,s); 5.0(1H,m), 7.42(1H,t,J=5 Hz); 8.70(2H,d,J=5 Hz).

The invention now being fully described, it will be apparent to one of ordinary skill in the art that many changes and modifications can be made thereto without departing from the spirit or scope of the invention as set forth herein.

What is claimed is:

1. An azetidine compound of the formula wherein R represents a hydroxyl group, and R$_a$, R$_b$, R$_c$, R$'_a$, R$'_b$ and R$'_c$ are identical or different and each represent a lower alkyl group.

* * * * *